United States Patent
Yoo

(10) Patent No.: US 9,279,818 B2
(45) Date of Patent: Mar. 8, 2016

(54) BIO DRIVE APPARATUS, AND ASSAY METHOD USING THE SAME

(75) Inventor: Jae Chern Yoo, Pohan-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 1992 days.

(21) Appl. No.: 11/988,069

(22) PCT Filed: Jun. 28, 2006

(86) PCT No.: PCT/KR2006/002524
§ 371 (c)(1),
(2), (4) Date: Jan. 29, 2009

(87) PCT Pub. No.: WO2007/001160
PCT Pub. Date: Jan. 4, 2007

(65) Prior Publication Data
US 2009/0163367 A1    Jun. 25, 2009

(30) Foreign Application Priority Data
Jun. 28, 2005    (KR) .................. 10-2005-0057513

(51) Int. Cl.
| G01N 31/00 | (2006.01) |
| G01N 35/00 | (2006.01) |
| G06F 19/00 | (2011.01) |
| G01N 33/48 | (2006.01) |
| G06F 19/10 | (2011.01) |

(52) U.S. Cl.
CPC ........ G01N 35/00069 (2013.01); G06F 19/702 (2013.01); *G06F 19/10* (2013.01)

(58) Field of Classification Search
CPC .................................................. G06F 19/702
See application file for complete search history.

(56) References Cited

U.S. PATENT DOCUMENTS

| 4,515,889 | A  |   | 5/1985 | Klose et al. |
| 6,377,894 | B1 |   | 4/2002 | Deweese et al. |
| 6,600,997 | B2 | * | 7/2003 | Deweese et al. ............ 702/22 |
| 8,211,038 | B2 | * | 7/2012 | Wang et al. ................ 600/584 |

FOREIGN PATENT DOCUMENTS

| JP | 11-500602 | 1/1999 |
| JP | 2000-171427 | 6/2000 |
| JP | 2000-515632 | 11/2000 |
| JP | 2002-521692 | 7/2002 |
| JP | 2002-282682 | 10/2002 |
| JP | 2003-084001 | 3/2003 |
| JP | 2004-020367 | 1/2004 |
| KR | 2000-0075815 | 12/2000 |
| KR | 10-2004-0004739 | 1/2004 |
| WO | 01/71328 A1 | 9/2001 |
| WO | 02/084302 A2 | 10/2002 |
| WO | 03/021223 | 3/2003 |
| WO | 03/080868 | 10/2003 |
| WO | 03/080868 A1 | 10/2003 |
| WO | WO 03/080868 | 10/2003 |
| WO | 2004/005919 A1 | 1/2004 |
| WO | WO 2004/005919 | 1/2004 |
| WO | WO 2004/065964 | 8/2004 |

OTHER PUBLICATIONS

Japanese Office Action received Jul. 13, 2010 in corresponding Japanese Patent Application No. 2008-519171.
European Search Report dated Apr. 21, 2011 in corresponding European Patent Application 06757743.7.
Korean Office Action issued on Aug. 13, 2009 in corresponding Korean Patent Application 10-2007-7025836.
Japanese Decision of Grant issued Jan. 17, 2012 in corresponding Japanese Patent Application 2008-519191.

* cited by examiner

*Primary Examiner* — Eric S Dejong
(74) *Attorney, Agent, or Firm* — Staas & Halsey LLP

(57) ABSTRACT

A non-optical bio-disc, a bio-disc device including the non-optical bio-disc and/or optical disc, a bio-driver apparatus in which a controller disc including a controller for the bio-disc is installed, and an assay method using the same, which are suitable for labs-on-a-chips for various diagnostic assays, nucleic acid hybridization assays, and immunoassays, are provided. The bio-driver apparatus is compatible with general optical discs, including audio, CD-ROMs, DVD players, etc. Thus, the bio-driver apparatus and the assay method offer and economical and convenient alternative to existing products. In addition, the bio-driver apparatus can be readily and easily applied in connection with a computer for remote diagnosis via the internet.

46 Claims, 8 Drawing Sheets

BIO DRIVE APPARATUS, AND ASSAY METHOD USING THE SAME

TECHNICAL FIELD

The present invention relates to an assay method using a bio driver and, more particularly, to a bio driver apparatus including: a controller which controls and drives a bio disc where a Lab-On-a-chip including various diagnosis and electro-chemical analysis devices is designed and arrayed and a general optical disc (CD and DVD); a strip insert slot into which a test strip for measurement of a bio sample and blood sugar is inserted; and a bio sensor for analyzing the test strip and an assay method using the bio driver apparatus.

BACKGROUND ART

The present invention is a continued application of International Patent Application No. PCT/KR02/00126, which was filed 27 Jan. 2002 and claims the priority of Korean Patent Application No. 10-2001-0003956, filed 27 Jan. 2001, and International Patent Application No. PCT/KR02/01035, which was filed 31 May 2002 and claims the priority of Korean Patent Application No. 10-2001-0031284, filed 31 May 2001. International Patent Application No. PCT/KR02/00126 and its priority Korean application are entitled "Nucleic acid hybridization assay method and device using cleavage technique responsive to complementary double strand or single strand of nucleic acids or oligonucleotides", International Patent Application No. PCT/KR02/01035 and its priority Korean application are entitled "Micro valve apparatus using micro bead and method for controlling the same", and Korean Patent Application No. 10-2005-0038765 entitled "Digital bio disc (DBD), DBD driver apparatus and assay method using the same". The disclosures of the above previous applications are incorporated herein by reference in their entirety.

The invention disclosed in the prior application provide a nucleic acid hybridization assay method and device using a cleavage technique responsive to a complementary double strand or single strand of-nucleic acids are applicable to diverse quantitative or qualitative assay devices. In addition, the micro valve is an essential element to control the flow of fluid in a lab-on-a-chip. In addition, the invention also provides a bio disc where the assay method and device are integrated in a disc and a bio driver apparatus including a bio optical pickup module device for driving and controlling the bio disc.

In addition, the invention disclosed in the prior application provide a nucleic acid assay device comprising a detector including an optical device, an electrochemical device, or a capacitance and impedance measurement device to detect or cleaved signal elements. The detected results can be digitized as computer executable software and provided through an established communications network, such as the Internet, to a patient or a doctor. In this manner, a remote diagnostic system ensuring convenience to both patient and doctor can be implemented based on the nucleic acid assay device. A capacitance and impedance measurement for the detector may include inter-digitated array electrodes with cleavable signal elements, as disclosed in the previous application.

Recently, various methods for analyzing bio samples including blood in medical fields have been proposed. Among them, a bio sensor using an enzyme analyzing method can be simply applied and obtain a rapid result with a good detection sensitivity, so that the bio sensor has been most widely used in hospitals and clinic assay laboratories. The enzyme analyzing method is mainly classified into a coloring method as a spectroscopic method and an electrode method as an electrochemical method. A bio sensor using the coloring method is disclosed in U.S. Pat. No. 4,509,859, entitled "Apparatus for optoelectronic evaluation of test strips" (Apr. 9, 1985). A bio sensor using the electrode method is disclosed in U.S. Pat. No. 4,655,880, entitled "Apparatus and method for sensing species, substances and substrates using oxidase" (Apr. 7, 1987).

As an example, there is a bio sensor for measuring blood sugar. In a blood sugar measuring technique using the coloring method, a blood measuring apparatus is designed to sense a change in color of a coloring matter due to glucose. A strip having a porous polymer membrane into which a reagent can easily permeate is used. As a currently representative test strip for the coloring method, SureStep of Lifescan Company and Glucotrend of Roche Company are commercially provided.

In the electrode method, instead of the coloring matter, an electric medium is used to measure electrons generated when an oxidizing enzyme of the glucose reacts with the electrode. In the method, since color is not measured, interference of red corpuscle does not occur. As a current representative electrochemical bio sensor, GlucoDr of All Medicus Company, Glucocard of Arkray Company, Accutrend Sensor of Roche Company, Precision QID of Abbott Company, and others are commercially provided.

Since the bio sensor using the coloring method can be easily implemented, the bio sensors for various bio samples have been developed. However, the bio sensor using the coloring method has a long measuring time in comparison with the bio sensor using the electrode method, and there is a measuring error caused from turbidity of the bio samples. Therefore, the bio sensor using the coloring method has difficulty in analyzing important bio samples.

The bio sensor using the electrode method has a short measuring time in comparison with the bio sensor using the coloring method, so that it can be easily used with high measurement accuracy. However, the bio sensors for various bio samples are not developed in comparison with the bio sensors using the coloring method, so that it can be used for only a few types of bio samples.

When the test strip for measuring bio sample and blood sugar is used, the measuring result can be obtained within a few second. In addition, the test strip can be easily purchased in the open market. In general, the test strip is manufactured in a disposable type and very inexpensive in comparison with a bio disc.

However, bio sample and blood sugar measuring apparatuses using a test strip has three shortcomings as follows. The shortcomings of the exemplified blood sugar measuring apparatus are described.

Firstly, prior to blood sugar measuring, an operator using blood sugar measuring apparatus should input a correction code number written in a strip container to blood sugar measuring apparatus by setting the button of blood sugar measuring apparatus or set a correction code to blood sugar measuring apparatus by using check strip (or test strip for correction). It is inconvenient for us to repeat this code setting operation again whenever one purchases strip newly.

Secondly, as a test sample for test strip, when requiring not whole blood, but serum or plasma, it is inconvenient to drive a centrifugal separator for obtaining these from whole blood and a separation process for extracting serum or plasma floated in the upside after the centrifugal separation. In addition, for the purpose of this, a separate centrifugal separator is required.

Thirdly, when analyzing various bio samples by using one measuring apparatus, it is usually inconvenient for us notify to the measuring apparatus of information about assayed material for analyzing by means of the button. For example, for blood sugar measuring apparatus, since main users of it are the old, even a very simple button operation is inconvenient for them. A code chip is developed to overcome such shortcomings. The manner using the code chip has a merit that it includes the information about assayed material to notify the measuring apparatus of much information about the test strip, but it has a shortcoming that a inconvenient process such as inserting the code chip into the measuring apparatus is required and a manufacturing cost of the code chip itself is high.

Fourthly, it has inconvenience that the measuring apparatus for coloring-method strip and the measuring apparatus for electrode-method strip are required separately.

To solve such problems, by arranging a perception electrode and a resistor on the strip, a patent that classify automatically whether the test strip in use is an electrode-method test strip or a coloring-method test strip to protocol accordingly by the measuring apparatus thereby to display an analyzing result in a liquid crystal display part is disclosed in Korean Patent Application Publication No. 10-2004-0004739 entitled "An apparatus for analyzing a bio sample quantitatively" and Korean Patent Application Publication No. 10-2001-0049234 entitled "An electrochemical bio chip having a perception electrode and an apparatus using the same". Such a perception electrode is arranged on the strip, and is read by the socket part of the measuring apparatus. When the strip is inserted into the socket part, the measuring apparatus perceives the types of the correction code and the analyzing material automatically by checking the state of the electrically contacted strip by the perception electrode.

However, for the contact type using the perception electrode, it is difficult to avoid a loss and an error due to mechanical wear of the socket part according to a frequent use of the strip. In addition, to classify various types of strips, the large number of the perception electrodes is required accordingly, and there is a problem that the perception electrode is complex and the design is limited accordingly.

However, since it is easy for us to separate serum and plasma from a bio disc by centrifugal force according to rotation, it is more efficient to use the bio disc than the strip in the diagnosis and assay requiring serum and plasma. However, since the bio disc includes various chemical processes, it takes a long time to obtain a analyzing and a measuring result, and the price of it is high compared to that of the strip.

In addition, for the assay site of the bio disc, the various types of the capture probes may be fixed to the assay site, and the number of the fixed array may be varied. Therefore, there may be the various types of the bio disc model or version. Therefore, to read the assay site accurately, a bio driver apparatus for controlling the bio disc should know exactly the model of the bio disc and the positional information and the array information for the assay site according to this.

Therefore, to manage diabetes effectively, since the blood sugar should be measured frequently, it is more efficient to use the strip than to use the bio disc in order to measure the blood sugar frequently within a short time. However, it is more efficient to use the bio chip in the analysis requiring serum or plasma as a test sample.

Therefore, a bio driver apparatus capable of driving both of the bio disc and the test strip is needed. In addition, strip IDs (identification) and product ID for identifying types of test strips and models and versions of bio discs are needed.

DISCLOSURE OF INVENTION

In order to solve the aforementioned problems, an object of the present invention is to provide a bio driver apparatus capable of driving and controlling both of a bio disc and a test strip.

Another object of the present invention is to provide a diagnosis and assay method with a bio disc and a diagnosis and assay method with a test strip by using the bio driver apparatus.

Hereinafter, the present invention will be described more clearly as follows.

According to an aspect of the present invention is provided a bio driver apparatus comprising: a controller for controlling driving of a general optical disc or a bio disc; a strip insert slot into which a test strip for measuring bio sample; and a bio sensor for assaying the test strip.

In the bio driver apparatus, the general optical disc includes a CD, a DVD, an audio CD, a CD-R, a game CD, or the like of which data can be optically read. The bio disc includes any disc device for assaying a bio sample which includes several reaction chambers and an assay site in a lab-on-a chip (see the prior application of the inventor). The bio sample includes blood sugar, cholesterol, or the like. At least one insert slot may be formed on a body of the bio driver. The bio driver apparatus can drive the general optical disc, the bio disc, or both of them. According to the present invention, replaying of the general optical disc and the diagnosis and assay of the bio sample based on the test strip can be performed. In addition to the diagnosis and assay based on the bio disc, the diagnosis and assay based on the test strip can be performed. In the bio driver apparatus, various types of cancer, blood sugar, cholesterol, various components in blood such as GOT and GPT can be qualitatively and quantitatively analyzed, and remote diagnosis can be performed.

In the bio driver apparatus, the bio disc may include: chambers which reserve a buffer or reaction solution; an assay site where bio materials specifically reacting with the bio sample are fixed and arrayed on a substrate; channels through which fluid flows between the chambers and the assay site; holes which connect the channels; and, valves which are used to opens and close the holes.

In the bio driver apparatus, the valve may include: a micro bead disposed in a hole; a permanent magnet disposed above the micro bead; and a movable permanent magnet disposed under the micro bead. For example, the valve is closed by an attractive force between the micro bead and a film-like permanent magnet disposed above the micro bead, and the hole of the valve is opened by an attractive force between the micro-bead and the moveable permanent magnet disposed under the micro-bead.

In the bio driver apparatus, the valves have different radial distances from the center of the bio disc. The movable permanent magnet is mounted on a radially movable slider disposed under the bio disc, so that the movable permanent magnet can be moved. As a result, the valves having different radial distances from the center of the bio disc can be addressed and independently controlled.

The bio driver apparatus may further comprise: a turntable on which the bio disc or the general optical disc is mounted; a spindle motor which rotates the bio disc or the general optical disc; a slider which includes a detector device for detecting an assay site in the bio disc and a permanent magnet for controlling opening and closing of the valves in the bio disc; a slide motor which controls moving of the slider; a central controller which controls whole components of the bio driver; and a body which supports the bio driver. The central control unit can be integrated into the controller of the present invention.

In the bio driver apparatus, the slider may be provided with a bio optical pickup module (BOPM) device where an optical sensor, an image sensor, or a fluorescent image sensor for detecting the assay site or product ID and a general optical pickup device (CD or DVD disk reader) are integrated as a module.

In the bio driver apparatus, the bio sensor may assay a coloring-method test strip and/or an electrode-method test strip.

In the bio driver apparatus, the coloring-method test strip may be any coloring-method test strip known in the related art. The coloring-method test strip includes a reaction region where a reagent which reacts with an assayed material and changes a color thereof is fixed. The coloring-method test strip includes a fluorescent strip. In the coloring method, gold conjugate or a fluorescent label such as Cy3 and Cy5 can bed used as a coloring material. The electrode-method test strip may be any electrode-method test strip known in the related art. In general, the electrode-method test strip includes a reference electrode, a working electrode, and a reaction region where the reagent is fixed.

In the bio driver apparatus, the bio sensor for assaying the coloring-method test strip may include: a light emitting device and a sensing device for measuring a change in color according to a reaction of a reagent on the coloring-method test strip and the bio sample; a A/D converter for converting a result of measurement into a digital value; and a central control unit which reads a digital signal output from the A/D converter.

In the bio driver apparatus, the bio sensor for assaying the electrode-method test strip may include: an A/D converter for converting a predetermined current generated from a working electrode according to a reaction of a reagent on the electrode-method test strip and the bio sample into a digital value; and a central control unit which reads a digital signal output from the A/D converter. The central control unit may be integrated into the central control unit of the bio driver.

In the bio driver apparatus, the bio sensor may be provided with a mount portion where the coloring-method test strip and the electrode-method test strip are mounted. The mount portion is an integrated type where two types of the strips can be selectively mounted.

In the bio driver apparatus, the bio sensor or the mounting portion further may include strip ID reading means for determining when the test strip is inserted into the strip insert slot and/or for reading strip ID.

In the bio driver apparatus, the correction code number, the type of strip, and the type of the assayed material may be indicated on the test strip by the strip ID (strip identification). The bio driver apparatus may further comprise strip ID reading means for automatically recognizing the strip ID at the time when the strip is inserted into the strip insert slot, thereby avoiding inconvenience of a manipulator to perform code setting operation and input information on the assayed material. In addition, due to the determination whether the strip ID exists, it is possible to determine whether the strip is inserted into the strip insert slot.

In the bio driver apparatus, the strip ID reading means may be constructed with an image sensor. In the bio driver apparatus, the image sensor may include a line image sensor and a light exposure means disposed in the vicinity of the line image sensor.

In the bio driver apparatus, the strip ID may be a bar code pattern printed on the test strip.

In the bio driver apparatus, the strip ID reading means may further include a central control unit which recognizes information such as a correction code number of the test strip, a type of the strip, and a type of an assayed material by using the strip ID. The central control unit may be integrated into the central control unit of the bio driver.

The strip may be a coloring-method strip or an electrode-method strip. The assayed material may be glucose, cholesterol, GPT, GOP, cancer marker, or the like. In addition, the strip smeared with urine is tested by using the optical sensor, so that a change in color of the strip can be seen. While blood is circulating through organs in a body, waste material and water during metabolism is filtered in a kidney, so that urine is excreted from the body. Therefore, when there is a functional disorder in kidney, urinary tract, urinary cyst, urethra, or other urine paths, the waste material may not be excreted, or the components of urine may change. In this case, the urine test for testing components of urine and abnormality thereof to diagnose diseases such as diabetes, kidney disease, and urinary tract infection is well known to the ordinarily skilled in the art. Materials which can be analyzed by using urine include urobilinogen, bilirubin, glucose, ketone, specific Gravity, occult blood, pH, protein, nitrite, leukocytes, or the like.

In the bio driver apparatus, the central control unit may control and drive the bio sensor according to a protocol associated with the correction code number of the test strip, the type of the strip, and the type of the assayed material.

In the bio driver apparatus, the controller or the bio optical pickup module (BOPM) device may further include product ID reading means for determining whether the bio disc is loaded or for identifying the product ID of the loaded bio disc. The product ID indicates a model or version of the bio disc.

In the bio driver apparatus, the product ID may be a bar code pattern printed on the bio disc.

In the bio driver apparatus, the product ID reading means may further include a central control unit which recognizes information such as a control protocol for the bio disc, an assay algorithm, a standard control value for reading the assay site, positional information on the assay site, and array information of the assay site by using the product ID.

In the bio driver apparatus may further comprise an input output device for providing the product ID or the strip ID to a computer and receiving a control command associated with the product ID or the strip ID from the computer.

In the bio driver apparatus, the input output device may be a USB (Universal Serial Bus) device or a device according to IEEE1394, ATAPI, or Internet communication standard.

In the bio driver apparatus, the computer may provide a control command associated with the product ID or the strip ID to the central control unit or a user interface (graphic user interface).

In the bio driver apparatus, the control command may include information such as control protocol for the bio disc, an assay protocol and algorithm for the test strip, a standard control value for reading the assay site, positional information on the assay site, and array information of the assay site.

In the bio driver apparatus, the user interface may include information on the assay algorithm, information on self diagnosis, device driver software, educational information for patients on clinical assays, and web sites and links enabling a patient to communicate with a doctor or hospital at a remote location based on his/her diagnosis result, or encrypted personal information.

In the bio driver apparatus, the computer may further include a wire or wireless network for downloading or updating device driver software for the bio driver apparatus.

In the bio driver apparatus, the computer may further include a monitor (display device) for providing a graphic user interface which displays a status of progress of main processes and steps of the bio driver apparatus in percentage (%) or as a bar graph or a pie graph or providing a graphic user interface which displays a statistical result of diagnosis and assay and performs remote diagnosis. Processes of the bio driver apparatus may mainly include a preparation process, a PCR process, a hybridization process, and an antigen-antibody reaction.

In the bio driver apparatus, the graphic user interface may further include statistic software for manages a result of reading quantitative analysis of the assay site or the test strip and a history thereof and provides information on periodic diagnosis to a user.

In the bio driver apparatus, the statistic software for history management may be driven by password registration and authentication at the time of diagnosis so as to perform the history management of the reading result for persons.

In the bio driver apparatus, the graphic user interface may further include software for measuring an intensity of a coloring light for the assay site of the bio disc and determining negative, positive, or dangerous group and calculating values thereof.

The bio driver apparatus according to claim 21, wherein the graphic user interface further includes software for determining negative, positive or dangerous group, or calculating values thereof based on the result of measurement obtained from the test strip.

In the bio driver apparatus, the graphic user interface may further include bio disc use history information providing means for performing history management of the product ID and providing information on how many times the currently loaded bio disc is used, information on a valid time, information on types of d disease which can be diagnosed, so that the information is provided to a user at the time of the bio disc being loaded.

In the bio driver apparatus, the graphic user interface may provide the bio disc use history information through the input output device to a central server.

In the bio driver apparatus, the micro bead may be a film-like cylindrical magnet.

In the bio driver apparatus, the valve may be coated with a rubber cushion material or constructed by inserting a film-like rubber cushion material between the micro bead and the hole. The rubber cushion material may be an elastic polymer such as a silicon rubber. Due to the cushion, the hole can be more hermetically closed. When the thin film cushion material is inserted between the micro bead and the hole, the film cushion material is inserted and assembled into an opening punctured at a position matching with the hole, so that the production process can be simplified.

In the bio driver apparatus, the slider may be connected to a slider motor with a worm gear so as to control a movement thereof.

The bio driver apparatus may further comprise disc type determining means for determining whether the disc loaded on the bio driver apparatus is a general optical disc or a bio disc.

In the bio driver apparatus, the bio optical pickup module (BOPM) device may read a groove pattern or a product ID pattern on a specific position of the bio disc so as to allow the central control unit to recognize that the disc currently loaded on the bio driver apparatus is the bio disc.

In the bio driver apparatus, the central control unit may determine whether the disc is a general optical disc or a bio disc, wherein, when the disc is the general optical disc, the central control unit transmits content of the optical disc from the optical pickup device to a storage unit of an output unit, transmits to-be-written content to the optical pickup device, or provides control signals for read and write to the components, and wherein, when the disc is the bio disc, the central control unit transmits control command signals for controlling the bio disc to the bio optical pickup module (BOPM) device.

In the bio driver apparatus, the image sensor or the fluorescent image sensor may be a line (one-dimensional) image sensor which senses light intensity in units of pixel. In the bio driver apparatus, the line image sensor may be a linear sensor array or a CIS (contact image sensor).

In the bio driver apparatus, the line image sensor may further include a light emitting diode (LED) for light exposure or fluorescence lighting and an optical lens which are disposed in the vicinity of the line image sensor, thereby constituting the bio optical pickup module (BOPM) device.

In the bio driver apparatus, the line (one-dimensional) image sensor may be moved on the slider to obtain two-dimensional image information of the assay site.

The bio driver apparatus may further comprise a light emitting diode (LED) for indicating that the bio disc is on operation. The LEDs may be blinked.

In the bio driver apparatus, the body which supports the bio driver may be constructed as a top loading type for the bio disc or a front loading type for the bio disc.

The bio driver apparatus may further comprise an eject button for ejecting the test strip from the inserted slot.

The bio driver apparatus may further comprise a liquid crystal display, so that the bio driver apparatus is used as a portable type.

The bio driver apparatus may further comprise a drawer for accommodating lancet tools.

According to another aspect of the present invention, there is provided an assay method using aforementioned the bio driver apparatus, comprising steps of: inserting the test strip into the strip insert slot; reading the strip ID on the test strip; performing diagnosis and assay of the bio sample on the strip according to the protocol corresponding to the read strip ID; and displaying a result of the diagnosis and assay.

According to still another aspect of the present invention, there is provided an assay method using aforementioned the bio driver apparatus, comprising steps of: loading the bio disc on the bio driver apparatus; reading the product ID on the bio disc; driving the bio disc according to the control protocol corresponding to the read product ID; analyzing the assay site by using the positional information of the assay site and the array information thereof according to the read product ID; and display a result of the diagnosis and analysis of the assay site.

The assay method may further comprise a step of displaying a statistical result of the diagnosis and analysis.

The assay method may further comprise steps of: transmitting the results to a doctor via a communication network; and performing a remote diagnosis between the doctor and a patient through remote communication.

The assay method may further comprise a step of determining whether the disc loaded on the bio driver apparatus is a bio disc or a general optical disc.

The assay method may further comprise a step of providing information on a valid time bead on the strip ID or the product ID to a user or informing a user that a bio disc and strip is expired and cannot be diagnosed or used. For example, a computer calculates production date of the bio disc and the test strip based on the barcode pattern and the current time and determines whether or not the diagnosis can be performed.

In the assay method, a statistical result of the diagnosis and analysis may be displayed in a graph which represents a change in blood sugar, cholesterol, GOT, GPT, or cancer marker or a change in component of a urine test according to time, so that tracing management can be performed.

The assay method may further comprise a step of ring a buzzer when the strip ID of the test strip inserted into the strip insert slot is read.

The assay method may further comprise a step of mounting serum or plasma centrifugally separated by using the bio disc on the test strip. For example, blood is mounted on the bio disc, and serum or plasma centrifugally separated from a preparation chamber by a high speed rotation is mounted on the test strip by using a syringe.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

The present invention will be described in detail in the following embodiments with reference to the appended drawings.

A bio-disc according to the present invention includes a valve which controls fluid flow or the flow rate in a lab-on-a-chip integrated in the bio-disc. The valve opens or closes a channel formed in the bio-disc using a microbead that is movable by the magnetic force generated by a permanent magnet and a movable permanent magnet disposed on the top and bottom surface of the bio-disc. International Patent Application No. PCT/KR02/01035 filed 31 May 2002 and its priority Korean Application No. 10-2001-0031284 filed 31 May 2002, which are entitled "Micro valve apparatus using microbead and method for controlling the same", can be referred to for the detailed structure of the valve.

In exemplary embodiments of the bio-disc according to the present invention, the microbead may include, for example, a magnetic ball, ferroelectric particles, paramagnetic particles, diamagnetic particles, a stainless steel ball. The microbead may be a spherical permanent magnet or a film-like cylindrical or rectangular permanent magnet. The film-like permanent magnet may have a thickness of, preferably, 0.1 mm-0.5 mm. Preferably, a film-like cushion material such as a silicon rubber may be inserted between the micro-bead and the hole.

Figure 1A:
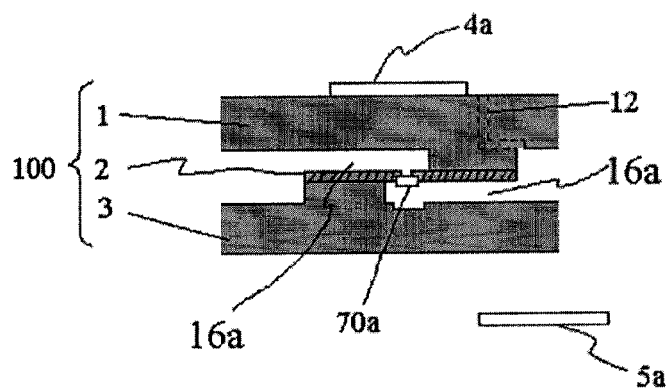
FIGS. 1A, 1B, and 1C shows an example of a cross section of a bio disc including a valve using a thin film cylindrical permanent magnet disposed in the bio disc.
Figure 1B:
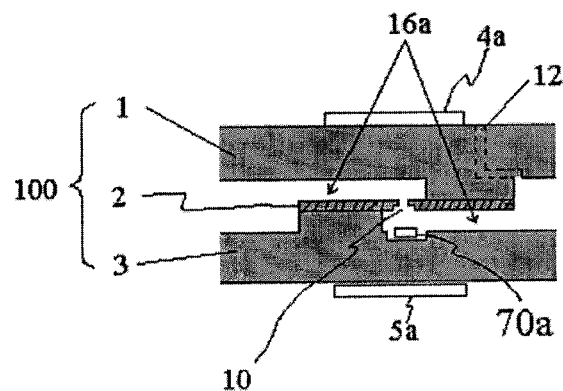
Figure 1C:
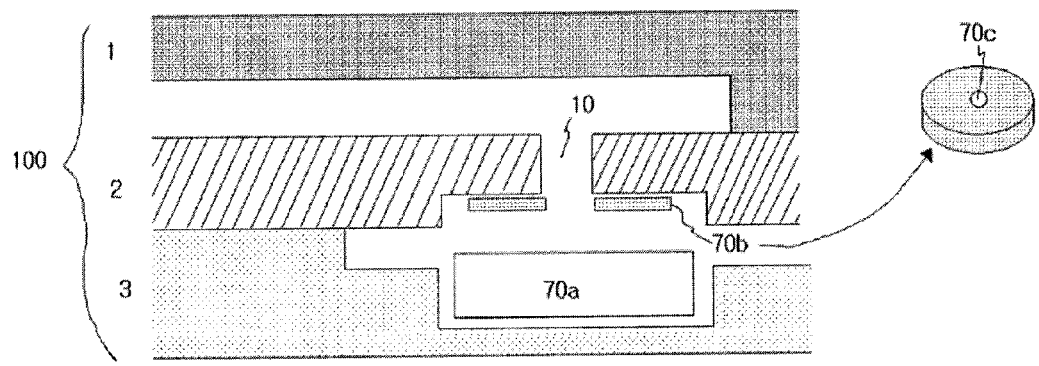

FIGS. 1a, 1b and 1c are sectional views of a bio-disc showing a valve apparatus therein using a permanent magnetic microbead 70a above which a permanent magnet 4a is disposed and under which a movable permanent magnet 5a is disposed.

As shown in FIG. 1a and 1b, a bio-disc 100 includes an upper substrate 1, an intermediate substrate 2, and a lower substrate 3. Channels as flow paths, chambers as buffer reservoirs, and holes connecting the channels are formed in each of the upper, intermediate, and lower substrates 1, 2, and 3 by injection molding. Next, the upper, intermediate, and lower substrates 1, 2, and 3 are bound together to form a body of the bio-disc 100.

FIG. 1a illustrates a state where a hole 10 is plugged by a permanent magnetic microbead 70a to block a channel 16a. FIG. 1b illustrates a state where the permanent magnetic microbead 70a is removed from the hole 10 to interconnect the channel 16a. To plug the hole 10 with the permanent magnetic microbead 70a and block the channel 16a, as shown in FIG. 1a, a movable permanent magnet 5a is removed from bottom surface (the center of the hole) of the bio-disc. In this case, the hole 10 is plugged by an attractive force between the micro-bead and a film-like permanent magnet 4a disposed above the micro-bead. In contrast, to open the hole 10 and interconnect the channel 16a, as shown in FIG. 1b, the movable permanent magnet 5a is moved to bottom surface (the center of the hole) of the bio-disc. In this case, the hole 10 is opened by an attractive force between the micro-bead and a movable permanent magnet 5a disposed under the micro-bead.

Since the bio-disc 100 according to the present invention includes the channel 16a, which is relatively narrow, as a fluid path, a ventilating hole 12 is formed in the upper substrate 1 to reduce the air pressure and allow a fluid to smoothly flow through the channel.

FIG. 1c is a sectional view of a bio-disc showing a valve apparatus wherein a film-like silicon rubber 70b is inserted between the permanent magnetic microbead 70a and the hole 10 in order to plug the hole 10 perfectly. The film-like silicon rubber 70b includes a hole 70c at the center which plays a role as a channel of fluid when opening the hole 10.

Figure 2A:
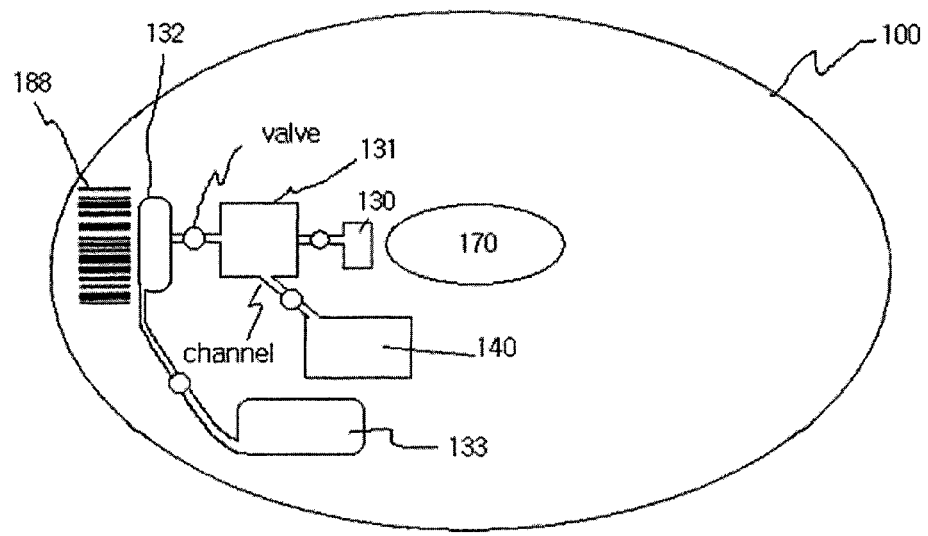
FIG. 2A shows a bio disc provided with a Lab-On-a-chip including chambers which reserve various buffers solution for assay and various chemical reactions are performed, channels through which processed fluid and buffer solutions flow, and valves for controlling closing and opening of the channels according to an embodiment of the present invention.

FIG. 2a illustrates a bio-disc 100, in which chambers as various assay buffer reservoirs and places for various reactions, channels as flow paths of a fluid sample and buffers, and valve apparatuses for controlling the opening and closing of the channels are integrated to form a lab-on-a-chip.

International Patent Application No. PCT/KR02/01035 filed 31 May 2002 and its priority Korean Patent Application No. 10-2001-0031284 filed 31 May 2001, which are entitled "Micro valve apparatus using microbead and method for controlling the same" can be referred to for the detailed structure of the valve apparatuses.

Opening and closing of the valves are independently controlled by approaching/separating movement of the movable permanent magnet disposed under the bio-disc 100. In FIG. 2a, reference numeral 170 denotes a disk hole, reference numeral 130 denotes a preparation chamber for preparing a bio sample directly from blood or cells, reference numeral 131 denotes a PCR chamber for polymerase chain reaction (PCR) or a label chamber for attaching a label marker, and reference numeral 132 denotes a chamber for hybridization or antigen-antibody reaction, which is an assay site with capture probes for analyzing and diagnosing amplified DNA products from the PCR or with immuno arrays immobilized thereon. Reference numeral 133 denotes a trash chamber for collecting wastes generated during washing. Reference numeral 140 denotes a chamber for reserving a washing buffer solution for washing, and reference numeral 188 denotes a barcode pattern which represents a product ID for discriminating models or versions of the bio-disc.

Figure 2B:
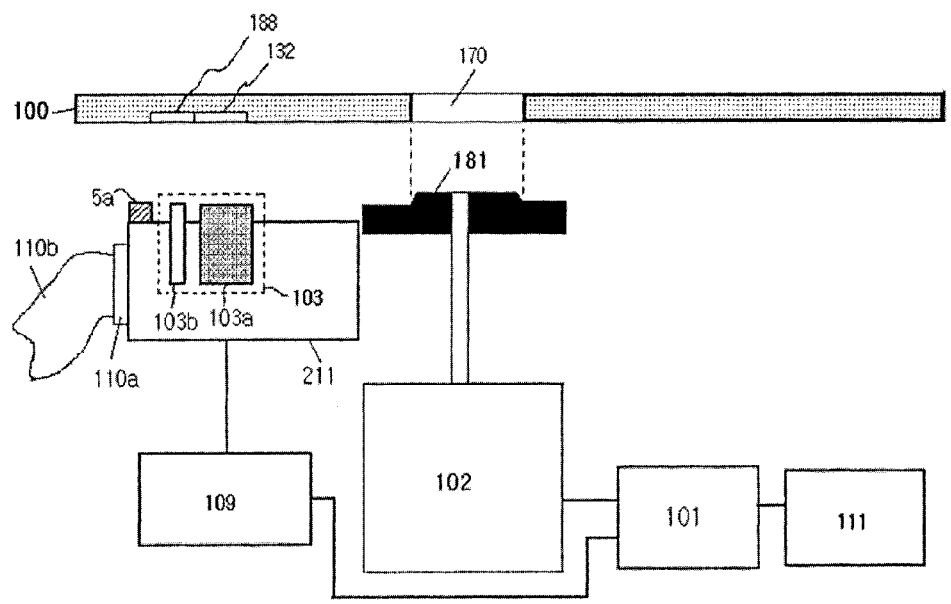
FIG. 2B shows a bio driver apparatus for driving and controlling a bio disc according to an embodiment of the present invention.

FIG. 2b illustrates a bio driver apparatus for controlling and operating the bio-disc 100. Reference numeral 211 denotes a slider on which a movable permanent magnet 5a is mounted, which is connected with and operated by a slide motor 109 to control the position of the movable permanent magnet 5a.

Opening and closing of the valve apparatuses at the start and ending points of time of each of the processes (preparation, PCR, hybridization, antigen-antibody reaction, and washing) are controlled by approaching/separating movement of the movable permanent magnet 5a mounted on slider 211. Fluid flow in the bio-disc 100 is induced by the centrifugal force generated as it is rotated. International Patent Application No. PCT/KR2006/001709 filed 28 Jun. 2006 and its priority Korean Patent Application No. 10-2005-0038765 filed 28 Jun. 2005, which are entitled "Digital bio disc (DBD), DBD driver apparatus, and assay method using the same" can be referred to for the detailed structure of the valve apparatuses.

Reference numeral 103a denotes an optical pickup device (a CD reader or a DVD reader) for reading a general optical disc (for example, an audio CD, a CR-R, a game CF, and a DVD). Reference numeral 103b denotes a detection device such as an image sensor, a optical sensor, or fluorescent image sensor. The optical pickup device 103a and the detection device 103b is combined in a module to provide a bio optical pickup module (BOPM) device 103.

In a case where reference numeral 103b in FIG. 3 is an image sensor, the image sensor may be a line image sensor, such as a linear sensor array or a CIS sensor, which senses optical intensity in pixel units and has a short focusing distance.

In the bio driver apparatus according to the invention, the BOPM device 103 is preferably combined with the movable permanent magnet 5a to control the opening and closing of the valves in a module.

In the bio driver apparatus according to the invention, the line image sensor may further include a light emitting diode (LED) for illumination or fluorescence light and an optical lens which are disposed in the vicinity of the line image sensor. Preferably, the LED may be a LED with a wavelength of from 500 nm to 800 nm or white LED. Preferably, the line image sensor may further include a intensity control unit for regulate the light exposure intensity of the LED. More preferably, the intensity control unit may differently regulate the intensity of the LED when detecting the assay site 132 and the product ID 188.

The BOPM device 103 including the line image sensor may be moved one by one steps on the slider 211 and collect line image informations to obtain two-dimensional image information of the assay site 132 and barcode pattern 188 on the bio-disc 100.

The bio driver apparatus according to the invention may preferably further comprise a central control unit 101 which generates several control signals for controlling an image sensor 103b to detect the assay site 132 and the product ID 188, a slide motor 109, an optical pickup device 103a to read a general optical disc, and a spindle motor 102.

Reference numeral 110b denotes a flexible cable to connect various control signals needed for the BOPM device 103 and is connected with the central control unit 101 via a wafer or harness 110a.

Reference numeral 181 denotes a turntable on which the bio-disc 100 or a general optical disc, such as an audio CD, a CD-R, a game CD, or a DVD, is loaded and which engages the disc hole 170 of the bio-disc 100 or a general optical disc. The bio-disc 100 is loaded on the turntable 181 in a top loading or front loading type. Reference numeral 111 denotes an input output device.

Figure 2C:
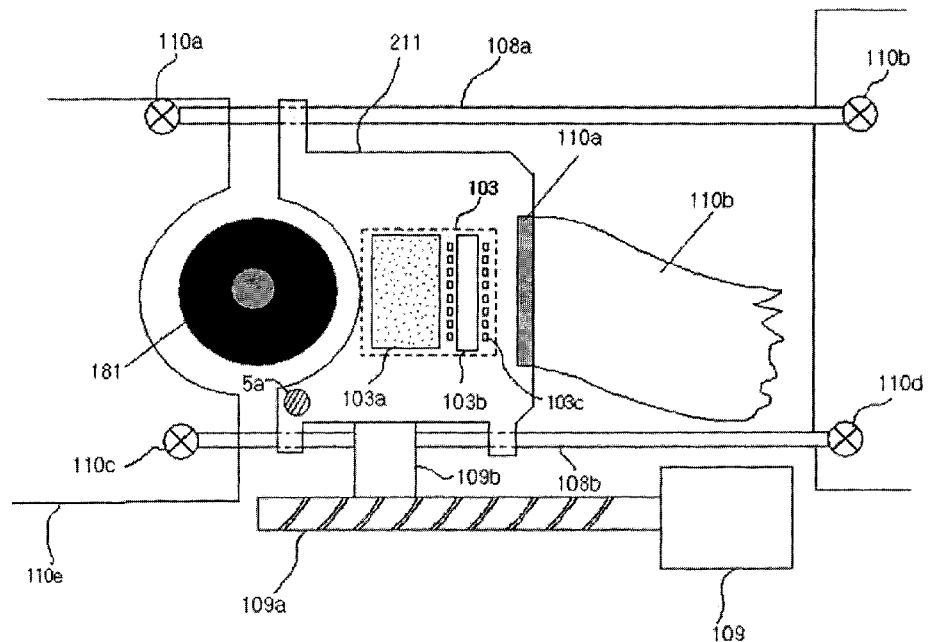
FIG. 2C shows an upper portion of a slider provided with a permanent magnet 5a and a bio optical pickup module (BOPM) device 103.

FIG. 2c illustrates an embodiment of slider 211 on which the BOPM device 103 and the movable permanent magnet 5a are mounted. The slider 211 is connected to the slide motor 109 through a worm gear 109a and its counter part 109b so that the moving thereof is controlled.

The slider 211 is moved in sliding on slide arms 108a and 108b as a guide. The slide arms 108a and 108b are connected with the body of the bio disc driver through screws 110a, 110b, 110c, 110d. Reference numeral 110b denotes a flexible cable to connect various control signals needed for the BOPM device 103 on the slider 211 and is connected with the central control unit via a wafer or harness 110a. Reference numeral 181 denotes a turntable which is rotated by the spindle motor. An optical pickup device 103a for reading a general optical disc, a movable permanent magnet 5a for controlling opening and closing of the valves, and an image sensor for detecting the assay site 132 and the product ID 188 are mounted on the slider 211. Reference numeral 103c denotes a LED for illumination which is disposed in the vicinity of the line image sensor 103b.

Figure 2D:
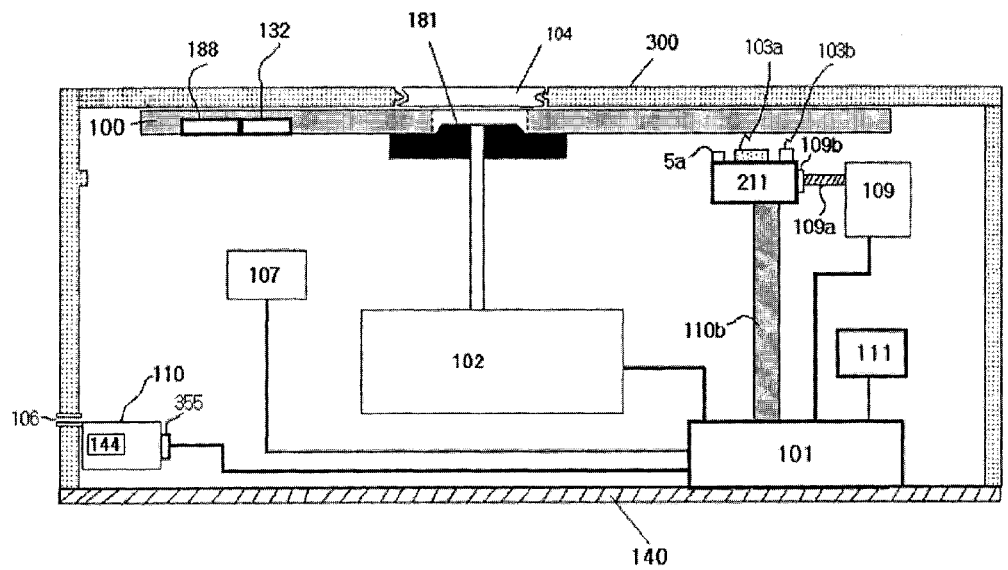
FIG. 2D shows an internal portion of a bio driver apparatus for driving and controlling a bio disc and being embedded with a bio sensor 110 for analyzing a test strip inserted into a strip insert slot.

FIG. 2d illustrates an embodiment of a bio-driver apparatus for controlling the bio-disc 100 which is loaded on the turntable 181 and assaying test strip using a bio sensor 110.

Reference numeral 300 denotes a body for supporting the bio driver. A circuit board 140 on which a central control unit 101 and a storage device or an input output device 111 are disposed is engaged with the bio driver body 300 as a base. The central control unit 101 controls the spindle motor 102 for rotating and stopping of the bio-disc 100 and the slide motor 109 for moving of the BOPM device 103 mounted on the slider, the permanent magnet 5a for opening and closing of the valves in the bio-disc, as well as the optical pickup device 103a for track searching and reading a general optical disc. On opening the valve, the permanent magnet 5a approaches the center of the hole in the bio-disc so closely that can exert an attractive force to the film-like cylindrical magnet 70a in the bio-disc effectively.

The results of a detection from the assay site 132 obtained by the image sensor 103b are transmitted to the central control unit 101 via the flexible cable 110b connected with the slider 211, or to a computer via the input output device 111.

Reference numeral 107 denotes a laser generation device which excites the fluorescent label of the coloring-method test strip. The detection of the fluorescent label excited by the laser generation device can be performed by the image sensor 103b.

The central control unit 101 determines whether a disc currently loaded into the bio-driver apparatus is a general optical disc, for example, an audio CD, CD-R, a game CD, or a DVD, or a bio-disc 100. If the currently loaded disc is determined to be a general optical disc, the central control unit 101 transmits information read from the optical disc using the optical pickup 103a to the input output device 111 or transmits information to be written to the optical pickup 103a and controls the operation of the optical disc using read/write control signals. If the currently loaded disc is determined to be a bio-disc 100, the central control unit 101 sends various control signals for controlling the lab-on-a-chip of the bio-disc to the corresponding each parts.

The bio driver apparatus according to the present invention may further comprise a bio-disc detection unit for the central control unit 101 to determine whether a disc currently loaded on the bio driver apparatus is a bio-disc 100 or a general optical disc selected from among an audio CD, a CD-R, a game CD, and a DVD.

In the bio driver apparatus according to the present invention, an optical pickup device on the BOPM 103 may read a groove pattern or an image sensor 103b may read a product ID 188 at a particular area on a surface of the bio-disc 100 to allow the central control unit 101 to recognize that a disc currently loaded on the bio driver is a bio-disc.

The bio driver apparatus according to the present invention may further comprises a strip ID reading means 144 for reading the strip ID of the test strip loaded into the strip slot 106 and a bio sensor 110 for assaying the test strip according to the corresponding strip ID.

In the bio driver apparatus according to the invention, the strip ID reading means 144 may further include a central control unit 101 which recognizes information such as a correction code number of the test strip loaded into the strip slot 106, a type of the strip (the coloring-method test strip and the electrode-method test strip), and a type of an assayed material (glucose, cholesterol, GPT, GOP, Cancer, etc.) by using the strip ID.

In the bio driver apparatus according to the invention, the central control unit 101 controls and drives the bio sensor 110 according to a protocol associated with the correction code number of the test strip, the type of the strip, and the type of the assayed material. The central control unit 101 and the bio sensor 110 are electrically connected each other via a harness or wafer 355.

The bio driver apparatus according to the invention may further comprise an input output device 111 for providing the detection results of the assay site 132, the product ID or the strip ID to a computer and receiving a control command associated with the product ID or the strip ID from the computer.

In the bio driver apparatus according to the invention, the computer may provide a control command associated with the product ID or the strip ID to the central control unit 101 or a user interface (graphic user interface).

In the bio driver apparatus according to the invention, the control command associated with the product ID or the strip ID may include information such as a control protocol for the bio disc 100, an assay algorithm of the test strip, a standard control value for reading the assay site, positional information on the assay site, and array information of the assay site.

In the bio driver apparatus according to the invention, the user interface may include information on the assay algorithm, information on self diagnosis, device driver software, educational information for patients on clinical assays, and web sites and links enabling a patient to communicate with a doctor or hospital at a remote location based on his/her diagnosis result, or encrypted personal information.

In the bio driver apparatus according to the invention, the input output device 111 may be a USB (Universal Serial Bus) device or a device according to IEEE1394, ATAPI, or Internet communication standard.

In the bio driver apparatus according to the invention, the computer may further include a wire or wireless network for downloading or updating device driver software for the bio driver apparatus. Reference numeral 104 denotes a disc pressing means for pressing the loaded disc.

Figure 3A:
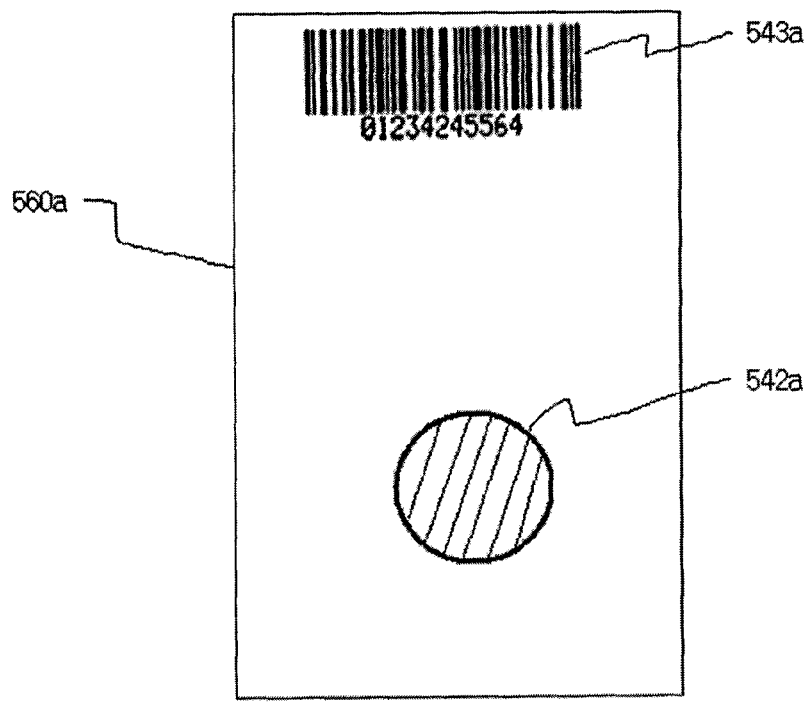
FIGS. 3A and 3B show test strips according to an embodiment of the present invention.
Figure 3B:
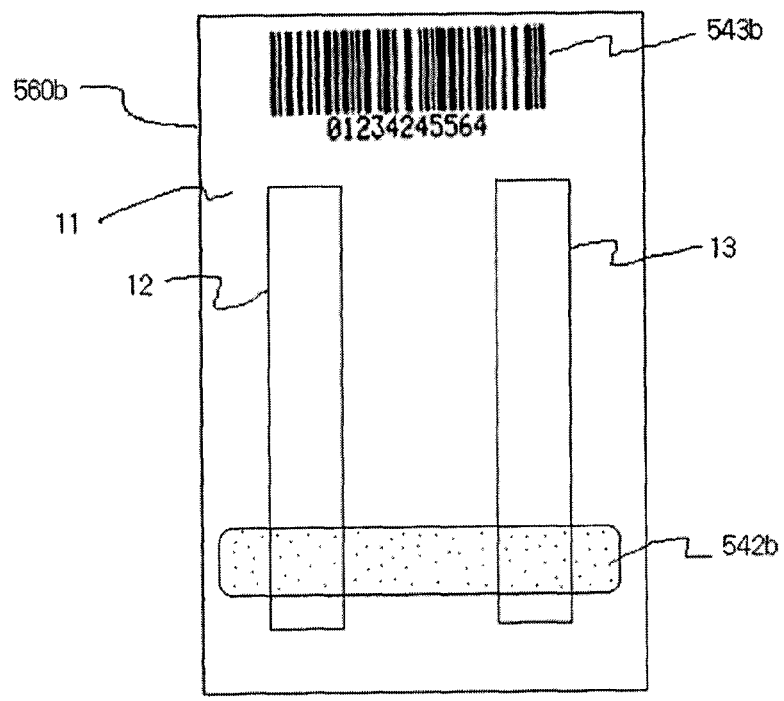

FIGS. 3A and 3B shows a test strip according to an embodiment of the present invention. Reference numerals 543a and 543b denote strip ID (strip identification) for representing types of the test strip (coloring-method strip and electrode-method strip), types of assayed materials (glucose, cholesterol, GOT, GPT, cancer, or the like), correction code, and the like. In addition, the central control unit 101 may analyze the strip ID to determine whether the strip is inserted into the strip insert slot. In the present invention, preferably, the strip ID is a barcode pattern.

FIG. 3A is a plan view showing a coloring-method test strip according to the present invention. A reagent which reacts with a to-be-assayed material contained in the bio sample is fixed in a reaction region 542a of the coloring-method test strip 560a. A change in color caused from a reaction of the reagent and the bio sample in the reaction region 542a is converted into a digital value by the bio sensor 110, and after that, analyzed in the central control unit 101.

FIG. 3B is a plan view showing an electrode-method test strip 560b according to the present invention. Reference numerals 12, 13, and 542b denote a reference electrode, a working electrode, and a reaction portion where the reagent is fixed. The electrode-method test strip 560b is constructed by forming the reference electrode 12 and the working electrode 13 on the insulator 11 and fixing the reagent 542b across the reference electrode 12 and the working electrode 13. In the working electrode 13, oxidation and reduction reactions of the to-be-assayed bio material and the reagent occur.

Due to an electro-chemical mechanism in the reaction of the bio sample and the reagent mounted on the test strip 560b, a predetermined current is generated from the working electrode 13. The current is converted into a digital value by the bio sensor 110, and after that, analyzed by the central control unit 101.

Figure 3C:
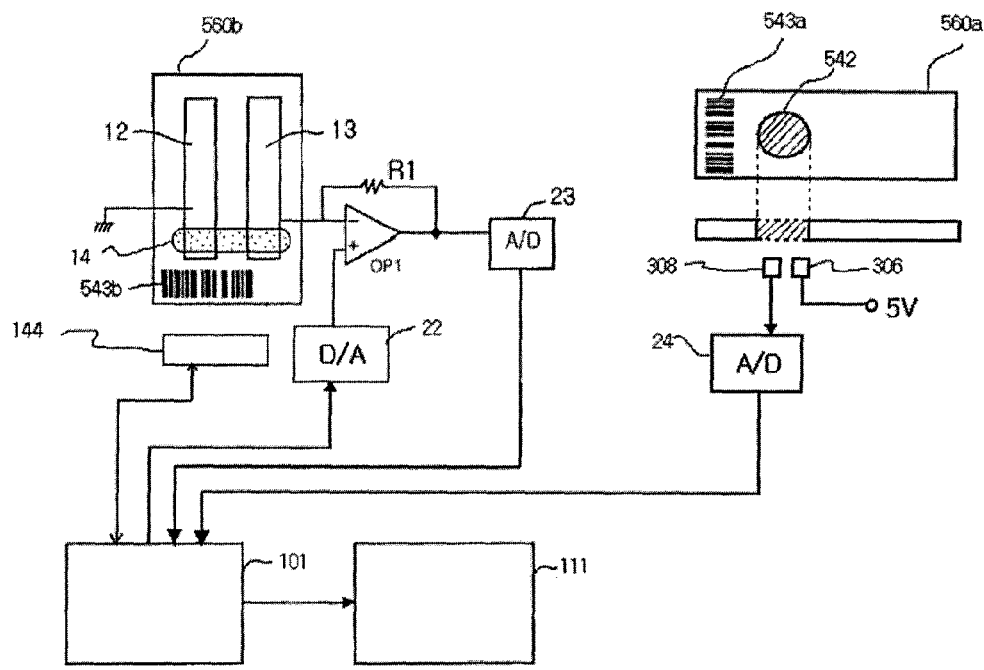
FIGS. 3C and 3D are a circuit diagram and a view for explaining operations of a bio sensor 110 according to an embodiment of the present invention.
Figure 3D:
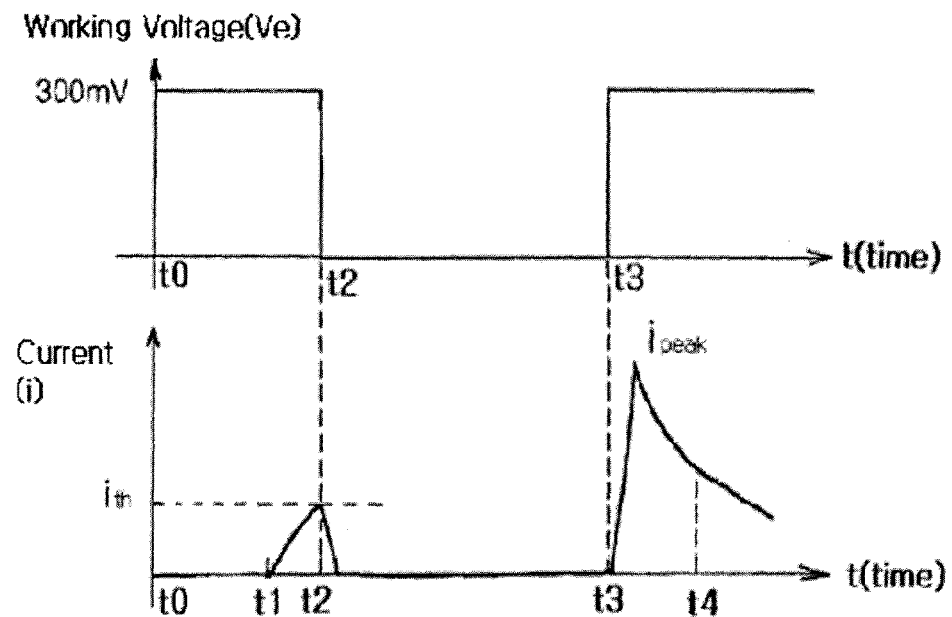

FIGS. 3C and 3D show a circuit and operations of the bio sensor 110 according to the present invention. The bio sensor can analyze the coloring-method test strip 560a and the electrode-method test strip 560b. In addition, the bio sensor includes strip ID reading means 144 for determining whether the test strip is inserted into the strip insert slot and for reading the strip ID.

When the test strip is inserted, the strip ID reading means 144 allows the central control unit 101 to recognize that the test strip is inserted. At the time of recognizing the insertion of the test strip, it is determined whether the inserted test strip is a coloring-method test strip or an electrode-method test strip.

Firstly, when the test strip is recognized to be the coloring-method test strip, the bio sensor detects an intensity of light which is emitted from a light emitting device 306 and reflected on the reaction region 542a with a photosensitive device 308 so as to measure a change in color of the coloring-method test strip 560a. A result of the measurement is converted into a digital value by an A/D converter 24. Next, the digital value is transmitted to the central control unit 10 and analyzed by a coloring-method measurement algorithm.

When the test strip is recognized to be the electrode-method test strip, at the recognition time t0, the central control unit 101 controls a D/A converter 22 to apply a working voltage Ve, for example, 300 mV, to the working electrode. According to a characteristic of an operational amplifier OP1, the applying of the working voltage Ve to the plus (+) terminal is equivalent to the applying of the working voltage Ve to the working electrode 13. At the time t1 when blood is mounted on the reaction portion 542b of the test strip, charges are generated from a reaction of the assayed material in blood and the reagent. Due to the voltage applied to the working electrode 13, the charges form a current i. As the reaction of the reagent and the assayed material proceeds, the current increases as shown in FIG. 3D. At the time t2 when the current increases up to a predetermined current value ith, the central control unit 101 set the working voltage Ve to 0V, so that no voltage is applied to the working electrode 13. Since the working voltage Ve is substantially 0V, the charges generated from the reaction of the assayed material and the reagent cannot flow through the working electrode 13, so that the charges are accumulated near the working electrode. An interval between the time t2 and the time t3 is generally referred to as an incubation time. The charges accumulated near the working electrode during the incubation time instantaneously flows through the working electrode 13 at the time t2 when the working voltage Ve is applied. As a result, a peak current ipeak occurs as shown in FIG. 3D. The current flowing through the working electrode 13 is converted into a voltage by a resistor R1 connected along a feedback loop between the output terminal and a minus (−) input terminal of the operational amplifier OP1. The converted voltage is converted into a digital signal by an A/D converter 23. The central control unit 101 stores data of correlation between a concentration of the assayed material in the sample and the current. The central control unit 101 reads a value of current flowing the working electrode at the time t4 after a predetermined time elapsing from the occurrence of the peak current ipeak so as to measure the concentration of the assayed material.

Reference numeral 22 denotes a D/A converter for converting the output of the central control unit 101 to an analog value to generate the working voltage Ve.

In a bio sensor using an electrode-method test strip including a regent which reacts with an assayed material of a mounted sample to generate positive charges corresponding to a concentration of the assayed material, the bio sensor includes: working voltage applying means 22 for applying a working voltage to an working electrode 13; voltage converting means for converting a current flowing through the working electrode 13 into a voltage; an amplifier for amplifying the voltage converted by the voltage converting means and outputting an analog voltage signal; an A/D converter 23 for converting the analog voltage signal generated from the amplifier into a digital voltage signal; and a central control unit 101. At the time t0 when the test strip is inserted into the strip insert slot 106, the central control unit 101 allow the working voltage applying circuit 22 to apply a first voltage (for example, 300 mV) to the working electrode.

At the time t2 after a predetermined time elapses from the time t1 when the sample is mounted, the central control unit 101 allows the working voltage applying circuit to apply 0V to the working electrode during a predetermined time interval. After that, at the time t3, the central control unit 101 allows the working voltage applying circuit to apply a second voltage (for example, 300 mV) to the working electrode 13. At the time t4 after a predetermined time elapses from the time when the second voltage is applied, the central control unit 101 reads the digital signal output from the A/D converter 23 to measure the concentration of the assayed material.

In the bio driver apparatus according to the present invention, preferably, the working voltage applying circuit 22 is a D/A converter.

In the bio driver apparatus according to the present invention, preferably, the strip ID reading means 144 is a line image sensor.

In the bio driver apparatus according to the present invention, preferably, the line image sensor is constructed by disposing LEDs (light emitting diodes) having a wavelength of 500 nm to 800 nm or white LEDs for light exposure of the line image sensor in the vicinity of the line image sensor.

Reference numeral 111 denotes an input output device 111 for providing a result of measurement of a concentration of the assayed material with respect to the test strip to a computer.

Figure 3E:
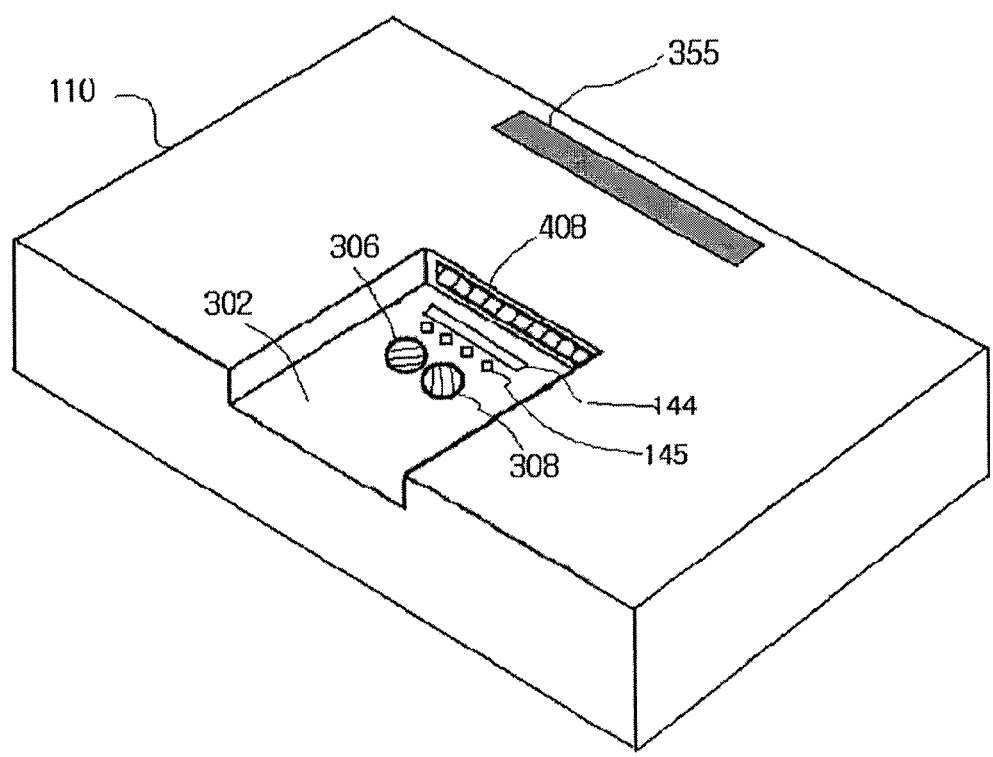
FIG. 3E shows a mount portion for connection of coloring-method and electrode-method test strips to a bio sensor when the coloring-method and the electrode-method test strips are inserted into a strip insert slot according to an embodiment of the present invention.

FIG. 3E shows a mounting portion 302 for connection of the coloring-method and electrode-method test strips to the bio sensor 110 when the coloring-method and electrode-method test strips are inserted into the strip insert slot according to an embodiment of the present invention.

The bio sensor 110 is constructed by integrating a mounting portion for the coloring-method test strip and a mounting portion of the electrode-method test strip. The mounting portion 302 is provided with a light emitting device 306 and a photosensitive device 308 for the coloring-method test strip and a socket portion 408 which is electrically connected to electrodes of the electrode-method test strip. The result of measurement obtained from the coloring-method test strip 560a by using the light emitting device 306 and the photosensitive device 308 is finally analyzed by the central control unit 101 based on a coloring-method protocol (analyzing method). The result of measurement obtained from the electrode-method test strip 560b by using the socket portion 408 is finally analyzed based on an electrode-method protocol (analyzing method). In addition, the mounting portion 302 is constructed with a line image sensor for reading the strip IDs 543a and 543b and a plurality of LEDs 145 for light exposure of the line image sensor disposed in the vicinity of the line image sensor.

Through the socket portion 408, the reference electrode 12 is electrically connected to ground, and the working electrode 13 is electrically connected to the minus (−) terminal of the operational amplifier OP1. The central control unit 101 and the bio sensor 110 are electrically connected to each other through a harness or a wafer 355.

Figure 4A:
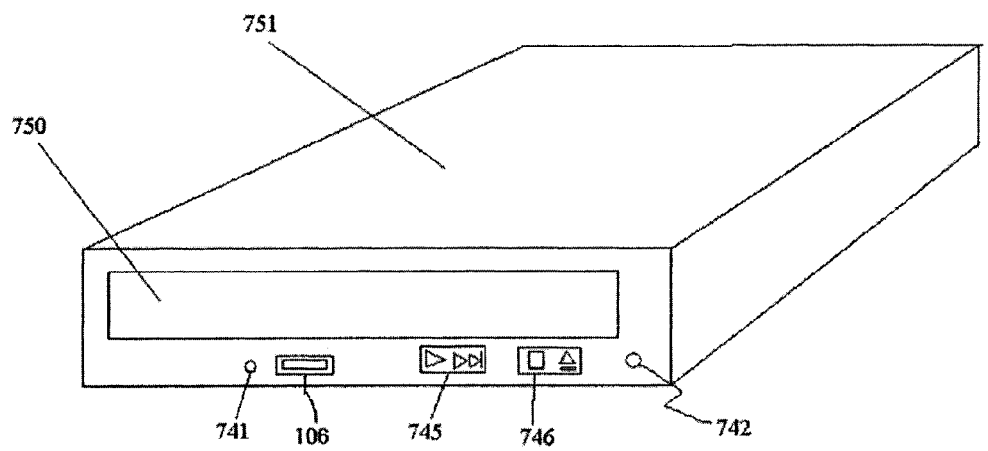
FIGS. 4A, 4B, and 4C show outer appearances of a front-loading type bio driver apparatus according to an embodiment of the present invention.
Figure 4B:
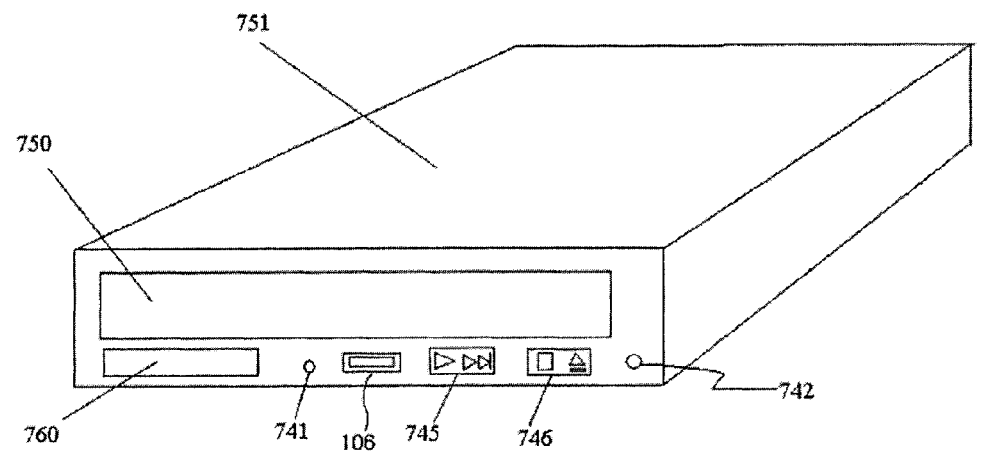
Figure 4C:
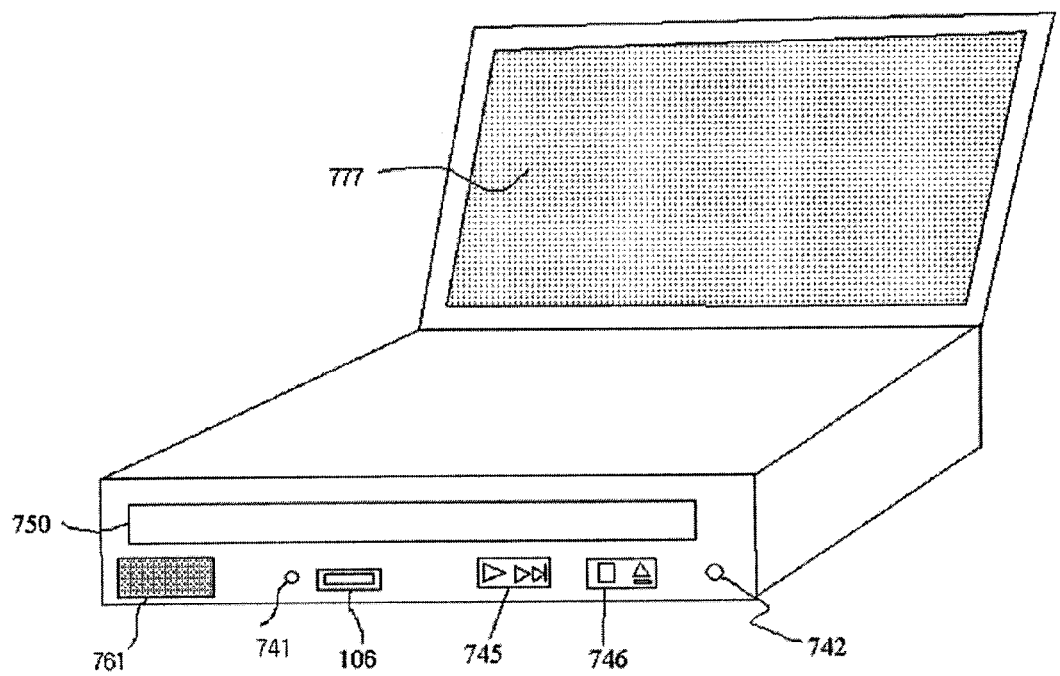

FIGS. 4a, 4b and 4c illustrate exemplary appearances of front loading-type bio-driver apparatuses according to the present invention. Reference numeral 751 denotes a case, reference numeral 750 denotes a bio-disc loading tray, reference numeral 106 denotes a strip slot for inserting the test strip, and reference 741 denotes an eject button for release the test strip inserted into the strip slot 106. Reference numerals 745 and 746 denote a play and search button and a stop button, respectively, for general optical discs. Reference numeral 742 denotes a blinking LED 742 for indicating in play of the bio driver apparatus.

FIG. 4b illustrates an embodiment of the bio driver apparatus indicating the status of proceeding with an assay through a liquid crystal display (LCD) 760.

FIG. 4c illustrates an embodiment of the bio driver apparatus further comprising a liquid crystal display 777, so that the bio driver apparatus is used as a portable type. Reference numeral 761 denotes a drawer for accommodating lancet tools.

In this embodiment, the status of progress in each main process, such as sample preparation, PCR, hybridization, and antigen-antibody reaction, can be expressed in percentages or as a bar graph using the displaying device 760, 777.

The status of proceeding with an assay in the bio drive apparatus according to the present invention can be displayed through a computer monitor or a graphic user interface. The status of progress in each main process, such as sample preparation, PCR, hybridization, and antigen-antibody reaction, can be expressed in percentages or as a bar or pie graph. The GUI may display a statistical result of the diagnosis and analysis.

While the present invention has been particularly shown and described with reference to exemplary embodiments thereof, it will be understood by those of ordinary skill in the art that various changes in form and details may be made therein without departing from the spirit and scope of the present invention as defined by the following claims.

Industrial Applicability

As described above, the present invention provides an assay method using a bio driver. More particularly, the present invention provides a bio driver apparatus including: a controller which controls and drives a bio disc where Lab-On-a-chip including various diagnosis and electro-chemical analysis devices is designed and arrayed and a general optical disc (CD and DVD); a strip insert slot into which a test strip for measurement of a bio sample and blood sugar is inserted; and a bio sensor for analyzing the test strip and an assay method using the bio driver apparatus.

The invention claimed is:

1. A bio disc driver apparatus comprising:
a bio disc comprising chambers which reserve one of a buffer and reaction solution, an assay site where bio materials specifically reacting with the bio sample are fixed and arrayed on a substrate, channels through which fluid flows between the chambers and the assay site;
a turntable on which the bio disc is loaded;
a spindle motor which rotates the bio disc by operating the turntable;
a slider disposed under the bio disc which includes a detector device for detecting the assay site in the bio disc;
a slide motor which radially moves the slider;
a strip insert slot into which a test strip for measuring bio sample is inserted;
a bio sensor for assaying the test strip; and
a controller configured to control the spindle motor and the slide motor, and to read an output from the bio sensor.

2. The bio disc driver apparatus according to claim 1, wherein the bio disc further includes:
holes which connect the channels; and,
valves which are used to open and close the holes.

3. The bio disc driver apparatus according to claim 2, wherein the valve includes:
a micro beads disposed in a hole; and
a permanent magnet disposed above the micro bead.

4. The bio disc driver apparatus according to claim 3, wherein the slider further comprising:
a permanent magnet for controlling opening and closing of the valves in the bio disc.

5. The bio disc driver apparatus according to claim 4, wherein the slider is provided with a bio optical pickup module (BOPM) device where an optical sensor, an image sensor, or a fluorescent image sensor for detecting the assay site or product ID.

6. The bio disc driver apparatus according to claim 1, wherein the bio sensor assays a coloring-method test strip and/or an electrode-method test strip.

7. The bio disc driver apparatus according to claim 6, wherein the bio sensor for assaying the coloring-method test strip includes:
a light emitting device and a sensing device for measuring a change in color according to a reaction of a reagent on the coloring-method test strip and the bio sample;
a A/D converter for converting a result of measurement into a digital value; and
a central control unit which reads a digital signal output from the A/D converter.

8. The bio disc driver apparatus according to claim 6, wherein the bio sensor for assaying the electrode-method test strip includes:
an A/D converter for converting a predetermined current generated from a working electrode according to a reaction of a reagent on the electrode-method test is strip and the bio sample into a digital value; and
a central control unit which reads a digital signal output from the A/D converter.

9. The bio disc driver apparatus according to claim 6, wherein the bio sensor is provided with a mount portion where the coloring-method test strip and the electrode-method test strip are mounted.

10. The bio disc driver apparatus according to claim 1, wherein the bio sensor or the mounting portion further includes strip ID reader to determine when the test strip is inserted into the strip insert slot and/or for reading strip ID.

11. The bio disc driver apparatus according to claim 10, wherein the strip ID reader is constructed with an image sensor.

12. The bio disc driver apparatus according to claim 11, wherein the image sensor includes a line image sensor and a light exposure means disposed in the vicinity of the line image sensor.

13. The bio disc driver apparatus according to claim 10, wherein the strip ID is a bar code pattern printed on the test strip.

14. The bio disc driver apparatus according to claim 10, wherein the strip ID reader further includes a central control unit which recognizes information such is as a correction code number of the test strip, a type of the strip, and a type of an assayed material by using the strip ID.

15. The bio disc driver apparatus according to claim 14, wherein the central control unit controls and drives the bio sensor according to a protocol associated with the correction code number of the test strip, the type of the strip, and the type of the assayed material.

16. The bio disc driver apparatus according to claim 5, wherein the controller or the bio optical pickup module (BOPM) device further includes product ID reader to determine whether the bio disc is loaded or for identifying the product ID of the loaded bio disc.

17. The bio disc driver apparatus according to claim 16, wherein the product ID is a bar code pattern printed on the bio disc.

18. The bio disc driver apparatus according to claim 16, wherein the product ID reader further includes a central control unit which recognizes information such as a control protocol for the bio disc, an assay algorithm, a standard control value for reading the assay site, positional information on the assay site, and array information of the assay site by using the product ID.

19. The bio disc driver apparatus according to claim 10, further comprising is an input output device for providing the product ID or the strip ID to a computer and receiving a control command associated with the product ID or the strip ID from the computer.

20. The bio disc driver apparatus according to claim 19, wherein the input output device is a USB (Universal Serial Bus) device or a device according to IEEE1394, ATAPI, or Internet communication standard.

21. The bio disc driver apparatus according to claim 19, wherein the computer provides a control command associated with the product ID or the strip ID to the central control unit or a user interface (graphic user interface).

22. The bio disc driver apparatus according to claim 21, wherein the control command includes information such as control protocol for the bio disc, an assay protocol and algorithm for the test strip, a standard control value for reading the assay site, positional information on the assay site, and array information of the assay site.

23. The bio disc driver apparatus according to claim 21, wherein the user interface includes information on the assay algorithm, information on self diagnosis, device driver software, educational information for patients on clinical assays, and web sites and links enabling a patient to communicate with a doctor or hospital at a remote location based on his/her diagnosis result, or encrypted personal information.

24. The bio disc driver apparatus according to claim 19, wherein the computer is further includes a wire or wireless network for downloading or updating device driver software for the bio driver apparatus.

25. The bio disc driver apparatus according to claim 19, wherein the computer further includes a monitor (display device) for providing a graphic user interface which displays a status of progress of main processes and steps of the bio driver apparatus in percentage (%) or as a bar graph or a pie graph or providing a graphic user interface which displays a statistical result of diagnosis and assay and performs remote diagnosis.

26. The bio disc driver apparatus according to claim 21, wherein the graphic user interface further includes statistic software for manages a result of reading quantitative analysis of the assay site or the test strip and a history thereof and provides information on periodic diagnosis to a user.

27. The bio disc driver apparatus according to claim 26, wherein the statistic software for history management is driven by password registration and authentication at the time of diagnosis so as to perform the history management of the reading result for persons.

28. The bio disc driver apparatus according to claim 21, wherein the graphic user interface further includes software for measuring an intensity of a coloring light for the assay site of the bio disc and determining negative, positive or dangerous group, or calculating values thereof.

29. The bio disc driver apparatus according to claim 21, wherein the graphic user interface further includes software for determining negative, positive or dangerous group, or calculating values thereof based on the result of measurement obtained from the test strip.

30. The bio disc driver apparatus according to claim 21, wherein the graphic user interface further includes bio disc use history information providing means for performing history management of the product ID and providing information on how many times the currently loaded bio disc is used, information on a valid time, information on types of d disease which can be diagnosed, so that the information is provided to a user at the time of the bio disc being loaded.

31. The bio disc driver apparatus according to claim 30, wherein the graphic user interface provides the bio disc use history information through the input output device to a central server.

32. The bio disc driver apparatus according to claim 3, wherein the micro bead is a film-like cylindrical magnet.

33. The bio disc driver apparatus according to claim 32, wherein the valve is coated with a rubber cushion material or constructed by inserting a film-like rubber cushion material between the micro bead and the hole.

34. The bio disc driver apparatus according to claim 4, wherein the slider is connected to a slider motor with a worm gear so as to control a movement thereof.

35. The bio disc driver apparatus according to claim 4, further comprising disc type determining means for determining whether the disc loaded on the bio driver apparatus is a general optical disc or a bio disc.

36. The bio disc driver apparatus according to claim 5, wherein the bio optical pickup module (BOPM) device reads a groove pattern or a product ID pattern on a specific position of the bio disc so as to allow the central control unit to recognize that the disc currently loaded on the bio driver apparatus is the bio disc.

37. The bio disc driver apparatus according to claim 5,
wherein the central control unit determines whether the disc is a general optical disc or a bio disc, wherein, when the disc is the general optical disc, the central control unit transmits content of the optical disc from the optical pickup device to a storage unit of an output unit, transmits to-be-written content to the optical pickup device, or provides control signals for read and write to the components, and
wherein, when the disc is the bio disc, the central control unit transmits bio control command signals for controlling the bio disc to the bio optical pickup module (BOPM) device.

38. The bio disc driver apparatus according to claim 5, wherein the image sensor or the fluorescent image sensor is a line (one-dimensional) image sensor which senses light intensity in units of pixel.

39. The bio disc driver apparatus according to claim 38, wherein the line image sensor is a linear sensor array or a CIS (contact image sensor).

40. The bio disc driver apparatus according to claim 38, wherein the line image sensor further includes a light emitting diode (LED) for light exposure or fluorescence lighting and an optical lens which are disposed in the vicinity of the line image sensor, thereby constituting the bio optical pickup module (BOPM) device.

41. The bio disc driver apparatus according to claim 38, wherein the line (one-dimensional) image sensor is moved on the slider to obtain two-dimensional image information of the assay site.

42. The bio disc driver apparatus according to claim 1, further comprising a light emitting diode (LED) for indicating that the bio disc is on operation.

43. The bio disc driver apparatus according to claim 4, wherein the body which supports the bio driver is constructed as a top loading type for the bio disc or a front loading type for the bio disc.

44. The bio disc driver apparatus according to claim 1, further comprising an eject button for ejecting the test strip from the inserted slot.

45. The bio disc driver apparatus according to claim 1, further comprising a liquid crystal display, so that the bio driver apparatus is used as a portable type.

46. The bio disc driver apparatus according to claim 45, further comprising a drawer for accommodating lancet tools.

\* \* \* \* \*